United States Patent
Borghese et al.

(10) Patent No.: US 7,381,826 B2
(45) Date of Patent: Jun. 3, 2008

(54) CRYSTALLINE FORMS OF {2-[1-(3,5-BIS-TRIFLUOROMETHYL-BENZYL)-5-PYRIDIN-4-YL-1H-[1,2,3]-TRIAZOL-4-YL]-PYRIDIN-3-YL}-(2-CHLOROPHENYL)-METHANONE

(75) Inventors: Alfio Borghese, Rue Granbonpre' (BE); David Scott Coffey, Indianapolis, IN (US); Pamela Kaye Footman, Indianapolis, IN (US); Steven Wayne Pedersen, Indianapolis, IN (US); Susan Marie Reutzel-Edens, Zionsville, IN (US); Shella Lenyonga Tameze, Indianapolis, IN (US); Carsten Timpe, Hamburg (DE); Carsten Weber, Hamburg (DE)

(73) Assignee: Eli Lilly and Company, Indianapolis, IN (US)

( * ) Notice: Subject to any disclaimer, the term of this patent is extended or adjusted under 35 U.S.C. 154(b) by 122 days.

(21) Appl. No.: 10/574,712

(22) PCT Filed: Oct. 12, 2004

(86) PCT No.: PCT/US2004/030914

§ 371 (c)(1),
(2), (4) Date: Apr. 5, 2006

(87) PCT Pub. No.: WO2005/042515

PCT Pub. Date: May 12, 2005

(65) Prior Publication Data

US 2007/0078166 A1    Apr. 5, 2007

(51) Int. Cl.
C07D 401/14    (2006.01)
A61K 31/535    (2006.01)

(52) U.S. Cl. ...................... 546/256; 514/333

(58) Field of Classification Search .................. 546/25, 546/256, 258; 514/333
See application file for complete search history.

(56) References Cited

U.S. PATENT DOCUMENTS

| 6,432,952 B1 | 8/2002 | Crocker et al. |
| 2002/0044971 A1 | 4/2002 | Amidon et al. |
| 2002/0099067 A1 | 7/2002 | Posanski |

FOREIGN PATENT DOCUMENTS

WO    WO 03/091226 A1    11/2003

OTHER PUBLICATIONS

Ni et al, "Solubilization and preformulation of carbendazim," *International Journal of Pharmaceutics*, vol. 244, pp. 99-104 (2002).

*Primary Examiner*—Janet L. Andres
*Assistant Examiner*—John Mabry
(74) *Attorney, Agent, or Firm*—R. Craig Tucker; Manisha A. Desai

(57) ABSTRACT

The present invention provides novel crystalline forms of {2-[1-(3,5-bistrifluoromethylbenzyl)-5-pyridin-4-yl-1H-[1, 2,3]triazol-4-yl]-pyridin-3-yl}-(2-chlorophenyl)-methanone, compositions thereof, intermediates thereof, methods of using the same, processes for making the same, and processes for making intermediates thereof.

19 Claims, No Drawings

CRYSTALLINE FORMS OF {2-[1-(3,5-BIS-TRIFLUOROMETHYL-BENZYL)-5-PYRIDIN-4-YL-1H-[1,2,3]-TRIAZOL-4-YL]-PYRIDIN-3-YL}-(2-CHLOROPHENYL)-METHANONE

The present invention relates to novel crystalline forms of {2-[1-(3,5-bis-trifluoromethyl-benzyl)-5-pyridin-4-yl-1H-[1,2,3]triazol-4-yl]-pyridin-3-yl}-(2-chlorophenyl)-methanone, processes for their preparation and isolation, novel intermediates, and pharmaceutical compositions comprising the crystalline forms of the invention. In addition, the present invention provides methods for treating disorders associated with an excess of tachykinins comprising administering to a patient in need thereof an effective amount of a crystalline compound of the present invention.

BACKGROUND OF THE INVENTION

The compound {2-[1-(3,5-bis-trifluoromethyl-benzyl)-5-pyridin-4-yl-1H-[1,2,3]triazol-4-yl]-pyridin-3-yl}-(2-chlorophenyl)-methanone was first described in U.S. Application No. 60/376,121 (PCT published application WO03/091226). Because the compound is an inhibitor of the NK-1 subtype of tachykinin receptor, the compound is useful for the treatment of disorders associated with an excess of tachykinins. For instance, the compound is useful for depression, including major depressive disorder; anxiety, including generalized anxiety disorder, panic disorder, obsessive compulsive disorder, and social phobia or social anxiety disorder; schizophrenia and other psychotic disorders, including bipolar disorder; neurodegenerative disorders such as dementia, including senile dementia of the Alzheimer's type or Alzheimer's disease; disorders of bladder function such as bladder detrusor hyper-reflexia and incontinence, including urge incontinence; emesis, including chemotherapy-induced nausea and acute or delayed emesis; pain or nociception; disorders associated with blood pressure, such as hypertension; disorders of blood flow caused by vasodilation and vasospastic diseases, such as angina, migraine, and Reynaud's disease; hot flushes; acute and chronic obstructive airway diseases such as adult respiratory distress syndrome, bronchopneumonia, bronchospasm, chronic bronchitis, drivercough, and asthma; inflammatory diseases such as inflammatory bowel disease; gastrointestinal disorders or diseases associated with the neuronal control of viscera such as ulcerative colitis, Crohn's disease, functional dyspepsia, and irritable bowel syndrome (including constipation-predominant, diarrhea-predominant, and mixed irritable bowel syndrome); and cutaneous diseases such as contact dermatitis, atopic dermatitis, urticaria, and other eczematoid dermatitis.

It is desired and advantageous to find a highly crystalline form of the compound that can be reproducibly and efficiently prepared on a commercial scale. During the development of an improved process for the synthesis of {2-[1-(3,5-bis-trifluoromethylbenzyl)-5-pyridin-4-yl-1H-[1,2,3]triazol-4-yl]-pyridin-3-yl}-(2-chlorophenyl)-methanone, we surprisingly discovered novel anhydrous polymorphs of the compound, hereinafter described as Form IV and Form V.

SUMMARY OF THE INVENTION

The present invention is related to a crystalline form of {2-[1-(3,5-bistrifluoromethylbenzyl)-5-pyridin-4-yl-1H-[1,2,3]triazol-4-yl]-pyridin-3-yl}-(2-chlorophenyl)-methanone, Form IV.

In another embodiment, the present invention relates to a second crystalline form of {2-[1-(3,5-bistrifluoromethylbenzyl)-5-pyridin-4-yl-1H-[1,2,3]triazol-4-yl]-pyridin-3-yl}-(2-chlorophenyl)-methanone, Form V.

The present invention also relates to a pharmaceutical composition comprising, as an active ingredient, Form IV or Form V, in combination with one or more pharmaceutically acceptable carriers, diluents, or excipients. In a preferred embodiment, the present invention relates to a pharmaceutical composition comprising Form IV, in combination with one or more pharmaceutically acceptable carriers, diluents, or excipients.

In a further embodiment, the present invention relates to a method of making compounds represented by Form IV or Form V. In addition, the present invention encompasses intermediates useful in making compounds represented by Form IV or Form V.

In a further embodiment, the present invention relates to methods for the treatment of a condition associated with an excess of tachykinins, comprising: administering to a patient in need thereof an effective amount of Form IV or Form V. That is, the present invention provides for the use of Form IV for the treatment of a disorder associated with an excess of tachykinins. In another embodiment, the present invention provides for the use of Form V for the treatment of a disorder associated with an excess of tachykinins.

In another aspect, the present invention provides Form IV or Form V for use in therapy. Furthermore, the present invention provides for the use of Form IV or Form V in the manufacture of a medicament for the treatment of a disorder associated with an excess of tachykinins.

In a preferred embodiment, the present invention provides a method for treating major depressive disorder, comprising: administering to a patient in need thereof an effective amount of Form IV.

In another preferred embodiment, the present invention provides a method for treating generalized anxiety disorder, comprising: administering to a patient in need thereof an effective amount of Form IV.

In another preferred embodiment, the present invention provides a method for treating panic disorder, comprising: administering to a patient in need thereof an effective amount of Form IV.

In another preferred embodiment, the present invention provides a method for treating obsessive-compulsive disorder, comprising: administering to a patient in need thereof an effective amount of Form IV.

In another preferred embodiment, the present invention provides a method for treating social phobia or social anxiety disorder, comprising: administering to a patient in need thereof an effective amount of Form IV.

In another preferred embodiment, the present invention provides a method for treating irritable bowel syndrome, comprising: administering to a patient in need thereof an effective amount of Form IV.

In another preferred aspect, the present invention provides a method for treating major depressive disorder, comprising: administering to a patient in need thereof an effective amount of Form V.

In another preferred embodiment, the present invention provides a method for treating generalized anxiety disorder, comprising: administering to a patient in need thereof an effective amount of Form V.

In another preferred embodiment, the present invention provides a method for treating panic disorder, comprising: administering to a patient in need thereof an effective amount of Form V.

In another preferred embodiment, the present invention provides a method for treating obsessive-compulsive disorder, comprising: administering to a patient in need thereof an effective amount of Form V.

In another preferred embodiment, the present invention provides a method for treating social phobia or social anxiety disorder, comprising: administering to a patient in need thereof an effective amount of Form V.

In another preferred embodiment, the present invention provides a method for treating irritable bowel syndrome, comprising: administering to a patient in need thereof an effective amount of Form V.

DETAILED DESCRIPTION OF THE INVENTION

A number of methods are available to characterize crystalline forms of organic compounds. For example, these methods include differential scanning calorimetry, thermogravimetric analysis, moisture sorption/desorption, $^{13}C$ Cross polarization/magic angle spinning (CP/MAS) nuclear magnetic resonance spectroscopy (solid-state NMR or SSNMR), and X-ray powder diffraction. Of these methods, X-ray powder diffraction and solid state NMR spectroscopy are very useful for identifying and distinguishing between crystalline forms, based on their long- and short-range order, respectively.

Analysis of each of these parameters indicates that the crystalline form of {2-[1-(3,5-bistrifluoromethylbenzyl)-5-pyridin-4-yl-1H-[1,2,3]triazol-4-yl]-pyridin-3-yl}-(2-chlorophenyl)-methanone originally resulting from the process described in U.S. Application No. 60/376,121 (WO03/091226) (Form I) is different than the two novel crystalline forms (Form IV and Form V) described herein. Variations in the characteristics of Form I versus Form IV or Form V are discussed in greater detail below.

X-Ray Powder Diffraction

X-ray powder diffraction patterns were obtained on a Siemens D5000 X-ray powder diffractometer, equipped with a CuK$_\alpha$ source ($\lambda$=1.54056 Å) and a Kevex solid-state Si(Li) detector, operating at 50 kV and 40 mA. Each sample was scanned between 3° and 40° in 2θ, with a step size of 0.02 in 2θ and a minimum scan rate of 9.0 second/step, with 1 mm divergence and receiving slits and a 0.1 mm detector slit.

It is well known in the crystallography art that for any given crystal form, the relative intensities and peak widths of the diffraction peaks may vary due to a number of factors, including the effects of preferred orientation and/or particle size. Preferred orientation effects can be minimized by methods well known in the art, including light grinding of the sample. Where the effects of preferred orientation and/or particle size are present, peak intensities may be altered, but the characteristic peak positions of the polymorph are unchanged. See, e.g., The United States Pharmacopeia #24, National Formulary #19, pages 1843-1844, 2000. Furthermore, it is also well known in the crystallography art that for any given crystal form, the angular peak positions may vary slightly. For example, peak positions can shift due to sample displacement or a variation in the temperature at which a sample is analyzed. Provided sample displacement errors are minimized, and the analysis is conducted at room temperature, a peak position variability of ±0.1° in 2θ (the angular precision of a typical laboratory diffractometer) will not hinder the identification of the crystalline forms of the present invention.

The angular peak positions in 2θ and corresponding relative intensity data (I/I$_o$) for all peaks with intensities equal to or greater than 5% of the largest peak for {2-[1-(3,5-bistrifluoromethylbenzyl)-5-pyridin-4-yl-1H-[1,2,3]triazol-4-yl]-pyridin-3-yl}-(2-chlorophenyl)-methanone are listed in the tables below.

Accordingly, using the methodology described above with CuK$_\alpha$ radiation, X-ray powder diffraction patterns were generated for Form I, the crystalline form resulting from the process described in U.S. Application No. 60/376,121 (WO03/091226), Example 132. The crystal form is characterized by the angular peak positions in 2θ and corresponding relative intensity data in Table I, which lists the 2θ values (±0.1° in 2θ) and relative intensities equal to or greater than 5% of the largest peak for Form I {2-[1-(3,5-bistrifluoromethylbenzyl)-5-pyridin-4-yl-1H-[1,2,3]triazol-4-yl]-pyridin-3-yl}-(2-chlorophenyl)-methanone:

TABLE I (Form I)

| Angle (°2θ) | I/I$_o$ (%) |
|---|---|
| 4.5 | 84.2 |
| 11.7 | 10.1 |
| 11.8 | 7.1 |
| 12.9 | 52.5 |
| 13.1 | 40.3 |
| 13.6 | 38.4 |
| 15.1 | 6.4 |
| 15.3 | 9.5 |
| 15.8 | 7.2 |
| 16.0 | 8.9 |
| 17.0 | 11.1 |
| 17.5 | 21.2 |
| 18.2 | 6.3 |
| 19.8 | 6.8 |
| 20.3 | 9.8 |
| 20.8 | 100.0 |
| 21.2 | 12.4 |
| 21.4 | 6.0 |
| 21.7 | 39.3 |
| 22.0 | 12.0 |
| 22.7 | 13.4 |
| 23.2 | 9.1 |
| 23.5 | 15.6 |
| 23.9 | 15.3 |
| 24.1 | 6.2 |
| 24.4 | 6.0 |
| 24.6 | 7.8 |
| 25.0 | 7.0 |
| 25.8 | 10.8 |
| 26.1 | 7.7 |
| 27.4 | 17.3 |
| 29.8 | 10.0 |
| 30.9 | 8.8 |
| 36.1 | 6.1 |
| 36.8 | 7.4 |

The present invention is directed to crystalline Form IV, characterized by the angular peak positions in 2θ and corresponding relative intensity data in Table II, which lists the 2θ values (±0.1° in 2θ) and relative intensities equal to or greater than 5% of the largest peak for Form IV {2-[1-(3,5-bistrifluoromethylbenzyl)-5-pyridin-4-yl-1H-[1,2,3]triazol-4-yl]-pyridin-3-yl}-(2-chlorophenyl)-methanone:

TABLE II

(Form IV)

| Angle (°2θ) | I/I_o (%) |
|---|---|
| 6.8 | 6.1 |
| 7.7 | 13.6 |
| 8.3 | 32.1 |
| 11.2 | 28.3 |
| 12.1 | 100.0 |
| 12.7 | 30.3 |
| 13.5 | 26.0 |
| 14.3 | 41.5 |
| 14.9 | 31.4 |
| 16.2 | 33.9 |
| 16.6 | 53.4 |
| 16.9 | 53.3 |
| 17.4 | 7.9 |
| 18.2 | 10.1 |
| 18.5 | 63.1 |
| 18.9 | 26.5 |
| 19.3 | 35.2 |
| 19.8 | 5.2 |
| 20.3 | 31.2 |
| 20.7 | 60.0 |
| 21.1 | 19.7 |
| 21.4 | 15.9 |
| 21.7 | 39.5 |
| 21.9 | 92.6 |
| 22.1 | 38.1 |
| 22.5 | 27.8 |
| 22.8 | 17.0 |
| 23.4 | 33.9 |
| 24.0 | 24.0 |
| 24.3 | 18.7 |
| 24.9 | 56.1 |
| 25.6 | 8.3 |
| 25.9 | 40.8 |
| 26.4 | 10.7 |
| 26.9 | 15.8 |
| 27.3 | 5.0 |
| 28.1 | 5.5 |
| 28.5 | 7.7 |
| 29.0 | 13.2 |
| 29.3 | 14.7 |
| 29.9 | 5.4 |
| 30.2 | 10.3 |
| 31.3 | 14.5 |
| 31.5 | 13.9 |
| 32.6 | 7.5 |
| 33.3 | 6.6 |
| 35.4 | 6.0 |
| 36.1 | 5.5 |
| 36.4 | 5.8 |
| 36.8 | 10.0 |

In a second embodiment, the present invention is directed to crystalline Form V, characterized by the angular peak positions in 2θ and corresponding relative intensity data in Table III, which lists the 2θ values (±0.1° in 2θ) and relative intensities equal to or greater than 5% of the largest peak for Form V {2-[1-(3,5-bistrifluoromethylbenzyl)-5-pyridin-4-yl-1H-[1,2,3]triazol-4-yl]-pyridin-3-yl}-(2-chlorophenyl)-methanone:

TABLE III

(Form V)

| Angle (°2θ) | I/I_o (%) |
|---|---|
| 7.9 | 10.7 |
| 11.2 | 11.2 |
| 12.5 | 100.0 |
| 13.1 | 12.1 |
| 14.0 | 10.8 |
| 15.8 | 32.5 |
| 16.3 | 10.0 |
| 16.5 | 33.2 |
| 17.4 | 19.5 |
| 17.6 | 7.3 |
| 18.7 | 7.9 |
| 18.9 | 13.1 |
| 19.1 | 61.8 |
| 19.7 | 33.6 |
| 20.9 | 61.1 |
| 21.5 | 67.5 |
| 21.7 | 29.8 |
| 22.2 | 14.6 |
| 22.5 | 5.2 |
| 23.5 | 36.4 |
| 24.2 | 39.4 |
| 25.3 | 13.3 |
| 25.6 | 54.8 |
| 27.4 | 28.2 |
| 27.7 | 12.1 |
| 28.6 | 18.1 |
| 30.0 | 7.2 |
| 31.8 | 7.0 |
| 32.3 | 6.8 |
| 32.6 | 5.0 |
| 38.7 | 9.6 |

Thus, a properly prepared crystalline sample of Form IV {2-[1-(3,5-bistrifluoromethylbenzyl)-5-pyridin-4-yl-1H-[1,2,3]triazol-4-yl]-pyridin-3-yl}-(2-chlorophenyl)-methanone may be characterized by X-ray diffraction pattern in 2θ values (±0.1° in 2θ) using CuK$_\alpha$ radiation having peaks as described in Table II. In particular, crystalline Form IV may be characterized by X-ray diffraction pattern in 2θ values (±0.1° in 2θ) using CuK$_\alpha$ radiation comprising at least one peak, which peak is at 14.3±0.1° in 2θ; alternatively, comprising at least one peak, which peak is at 12.1±0.1° in 2θ; more particularly, comprising at least two peaks wherein one peak is 12.1±0.1°, and the second peak is selected from the group consisting of 7.7±0.1°, 8.3±0.1°, 12.7±0.1°, 13.5±0.1°, 14.3±0.1°, 14.9±0.1, 16.6±0.1°, 16.9±0.1°, 18.5±0.1°, 21.9±0.1°, and 24.9±0.1° in 2θ; more particularly, comprising at least two peaks wherein one peak is 12.1±0.1°, and the second peak is selected from the group consisting of 8.3±0.1°, 14.3±0.1°, 14.9±0.1°, 16.6±0.1°, 16.9±0.1°, 18.5±0.1°, 19.3±0.1°, 21.9±0.1°, and 24.9±0.1° in 2θ; more particularly, comprising at least two peaks wherein one peak is 12.1±0.1°, and the second peak is selected from the group consisting of 8.3±0.1°, 14.3±0.1°, 16.6±0.1°, 16.9±0.1°, and 18.5±0.1° in 2θ; more particularly, comprising at least the following peaks: 12.1±0.1014.3±0.1°, 16.6±0.1°, and 18.5±0.1° in 2θ; more particularly, comprising at least the following peaks: 8.3±0.1°, 12.1±0.1°, 16.6 0.1°, 16.9±0.1°, and 18.5±10.1°; more particularly, comprising at least the following peaks: 8.3±0.1°, 12.1±0.1°, 12.7±0.1°, 13.5±0.1°, 14.3±0.1°, 14.9±0.1°, 16.9±0.1°, 18.5±0.1, and 24.9±0.1° in 2θ; more particularly, comprising at least the following peaks: 7.7±0.1°, 8.3±0.1°, 12.1±0.1°, 12.7±0.1°, 13.5±0.1°, 14.3±0.1°, 14.9±0.1°, 16.6±0.1°, 16.9±0.1°, 18.5±0.1°, 21.9±0.1°, and 24.9±0.1° in 2θ.

In a second embodiment of the present invention, a properly prepared crystalline sample of Form V {2-[1-(3,5-bistrifluoromethylbenzyl)-5-pyridin-4-yl-1H-[1,2,3]triazol-4-yl]-pyridin-3-yl}-(2-chlorophenyl)-methanone may be characterized by X-ray diffraction pattern in 2θ values (±0.1° in 2θ) using CuK$_\alpha$ radiation having peaks as described in Table III, and in particular, comprising at least one peak, which peak is at 12.5±6.1° in 2θ; more particularly, comprising at least two peaks wherein one peak is 12.5±0.1°, and the second peak is selected from the group consisting of 7.9±0.1°, 11.2±0.1°, 13.1±0.1°, 14.0±0.10°, 15.8±0.10°, 19.1±0.1°, 19.7±0.1°, 20.9±0.1°, 21.5±0.1°, and 25.6±0.1° in 2θ; more particularly, comprising at least two peaks wherein one peak is 12.5±0.1°, and the second peak is selected from the group consisting of 15.8±0.1°, 16.5±0.1°, 19.1±0.1°, 19.7±0.1°, 21.5±0.1°, 25.3±0.1°, 27.7±0.1°, and 28.6±0.1° in 2θ; more particularly, comprising at least the following peaks: 12.5±0.1°, 25.3±0.1°, and 27.7±0.1° in 2θ; more particularly, comprising at least the following peaks: 12.5±0.1°, 25.3±0.1°, 27.7±0.1°, and 28.6±0.1° in 2θ; more particularly, comprising at least the following peaks: 12.5±0.1°, 15.8 10.1°, 16.5±0.1°, 19.1±0.1°, and 19.7±0.1° in 2θ; more particularly comprising at least the following peaks: 7.9±0.1°, 12.5±0.1°, 13.1±0.1°, 14.0±0.1°, 15.8±0.1°, 19.1±0.1°, 19.7±0.1°, and 25.6±0.1° in 2θ; more particularly, comprising at least the following peaks: 7.9±0.1°, 12.5±0.1°, 13.1±0.1°, 14.0±0.1, 15.8±0.1°, 16.5±0.1, 19.1±0.1°, 19.7±0.1°, and 25.6±0.1° in 2θ; most particularly, comprising at least the following peaks: 7.9±0.1°, 11.2±0.1°, 12.5±0.1°, 13.1±0.1°, 14.0±0.1°, 15.8±0.1°, 19.1±0.1°, 19.7±0.1°, 20.9±0.1°, 21.5±0.1°, and 25.6±0.1° in 2θ.

$^{13}$C Solid State Nuclear Magnetic Resonance (NMR)

$^{13}$C Cross polarization/magic angle spinning (CP/MAS) NMR (solid-state NMR or SSNMR) spectra were obtained using a Varian Unity Inova 400 MHz NMR spectrometer operating at a carbon frequency of 100.573 MHz and equipped with a complete solids accessory and a Chemagnetics 4.0 mm T3 probe. Ramped-amplitude cross-polarization (RAMP-CP) at 62 kHz and two-pulse phase modulation (TPPM) decoupling at 70 kHz were used. Acquisition parameters were as follows: 90° proton radio frequency pulse width 4.0 μs, contact time 2.0 ms, pulse repetition time 10 s, MAS frequency 10 kHz, spectral width 50 kHz, and acquisition time 50 ms. Chemical shifts were referenced to the methyl group of hexamethylbenzene (δ=17.3 ppm) by sample replacement. The analysis is conducted at room temperature. All values are provided in parts per million (ppm) and have a peak position variability of ±0.2 ppm.

The spectrum for Form I {2-[1-(3,5-bistrifluoromethylbenzyl)-5-pyridin-4-yl-1H-[1,2,3]triazol-4-yl]-pyridin-3-yl}-(2-chlorophenyl)-methanone comprises isotropic peaks at the following chemical shifts: 52.8±0.2, 121.0±0.2, 122.8±0.2, 125.4±0.2, 128.7±0.2, 130.9±0.2, 134.5±0.2, 136.4±0.2, 138.0±0.2, 139.6±0.2, 145.3±0.2, 150.1±0.2, 151.0±0.2, and 194.1±0.2 ppm.

Thus, the present invention is directed to Form IV {2-[1-(3,5-bistrifluoromethylbenzyl)-5-pyridin-4-yl-1H-[1,2,3]triazol-4-yl]-pyridin-3-yl}-(2-chlorophenyl)-methanone, which comprises isotropic peaks at the following chemical shifts: 52.3±0.2 and 195.4±0.2 ppm. More preferably, the invention is directed to Form IV, which comprises isotopic peaks at the following chemical shifts: 52.3±0.2, 123.5±0.2, 127.2±0.2, 131.4±0.2, 133.5±0.2, 136.9±0.2, 146.7±0.2, 149.3±0.2, 151.4±0.2, and 195.4±0.2 ppm. Most preferably, the invention is directed to Form IV, which comprises isotropic peaks at the following chemical shifts: 52.3±0.2, 123.5±0.2, 127.2±0.2, 129.6±0.2, 131.4±0.2, 133.5±0.2, 135.4±0.2, 136.9±0.2, 146.7±0.2, 149.3±0.2, 151.4±0.2, and 195.4±0.2 ppm.

In another embodiment, the present invention is directed to Form V {2-[1-(3,5-bistrifluoromethylbenzyl)-5-pyridin-4-yl-1H-[1,2,3]triazol-4-yl]-pyridin-3-yl}-(2-chlorophenyl)-methanone, which comprises isotropic peaks at the following chemical shifts: 54.3±0.2 and 196.6±0.2 ppm. More preferably, the invention is directed to Form V, which comprises isotropic peaks at the following chemical shifts: 54.3±0.2, 123.7±0.2, 127.4±0.2, 132.0±0.2, 134.3±0.2, 137.1±0.2, 145.8±0.2, 151.0±0.2, and 196.6±0.2 ppm. Most preferably, the invention is directed to Form V, which comprises isotopic peaks at the following chemical shifts: 54.3±0.2, 123.7±0.2, 127.4±0.2, 130.1±0.2, 132.0±0.2, 134.3±0.2, 137.1±0.2, 145.8±0.2, 149.1±0.2, 151.0±0.2, and 196.6±0.2 ppm.

The following examples further illustrate processes for preparing the compound, {2-[1-(3,5-bistrifluoromethylbenzyl)-5-pyridin-4-yl-1H-[1,2,3]triazol-4-yl]-pyridin -3-yl}-(2-chlorophenyl)-methanone, as well as crystalline Form IV and Form V. The examples are not intended to be limiting to the scope of these processes in any respect.

In preparing the compound {2-[1-(3,5-bistrifluoromethylbenzyl)-5-pyridin-4-yl-1H-[1,2,3]triazol-4-yl]-pyridin-3-yl}-(2-chlorophenyl)-methanone, the reaction is carried out by mixing the novel intermediate, (2-chlorophenyl)-[2-(2-hydroxy-2-pyridin-4-yl-vinyl)pyridin-3-yl]methanone or a salt thereof, preferably, its phosphate salt, with 1-azidomethyl-3,5-bistrifluoromethylbenzene and a suitable base in the presence of a solvent. Bases that may be used in the reaction include potassium hydroxide, potassium bicarbonate, sodium bicarbonate, potassium phosphate monohydrate, sodium carbonate, sodium phosphate dodecahydrate, or sodium ethoxide, with potassium carbonate as a preferred base. Useful solvents for the reaction include DMSO, isopropanol, ethanol, THF, and toluene. Preferably, the reaction is carried out in DMSO or isopropanol. The reaction temperature is not critical, but may preferably vary from approximately 40° C. to approximately 80° C.

The product of the reaction can be isolated and purified by techniques well known in the art, such as precipitation, filtration, extraction, evaporation, trituration, chromatography, or recrystallization.

In preparing the crystalline forms of the present invention, the use of an anti-solvent may be advantageous. As used in the context of the present process, the term "anti-solvent" refers to a solvent in which {2-[1-(3,5-bistrifluoromethylbenzyl)-5-pyridin-4-yl-1H-[1,2,3]triazol-4-yl]-pyridin-3-yl}-(2-chlorophenyl)-methanone is significantly less soluble relative to the selected solvent. Preferably, when an anti-solvent is used, it is miscible with the selected solvent.

Thus, {2-[1-(3,5-bistrifluoromethylbenzyl)-5-pyridin-4-yl-1H-[1,2,3]triazol-4-yl]-pyridin-3-yl}-(2-chlorophenyl)-methanone (Form IV and Form V) may be prepared by crystallization from a solvent under controlled conditions. Crystallization from solution and/or by solution-mediated phase transformations (slurrying techniques) is contemplated to be within the scope of the present process.

In practice, a number of solvents and anti-solvents have been found to be useful in the preparation of Form IV. These solvents include lower alcohols, ethers, esters, nitriles, and halocarbons. For example, Form IV of the present invention can be prepared by crystallization from a solvent selected from the group consisting of isopropanol, acetone, acetonitrile, propanol, butanol, ethyl acetate, methyl tertiary butyl ether, and dichloromethane. A preferred solvent from which Form IV may be crystallized is isopropanol. Anti-solvents such as hexanes, heptane, or water may also be useful for the crystallization of Form IV.

Form IV may be prepared over a range of temperatures. In practice, Form IV may be prepared at temperatures ranging from room temperature to about 85° C.

Form V of the present invention may also be prepared by crystallization from a solvent. For example, Form V may be crystallized from an aqueous organic solvent mixture. In practice, the organic solvent useful for crystallization of Form V is a lower alcohol, such as methanol or ethanol, and the anti-solvent is water.

Crystallization of Form V may also be carried out at temperatures ranging from room temperature to approximately 76° C.; more preferably from 68-71° C.

One of ordinary skill in the art will recognize that an alternate name for the crystalline compounds of Form IV and Form V is: Methanone, [2-[1-[[3,5-bis(trifluoromethyl)phenyl]methyl]-5-(4-pyridinyl)-1H-1,2,3-triazol-4-yl]-3-pyridinyl](2-chlorophenyl)-.

The terms and abbreviations used in the preparations and examples have their normal meanings unless otherwise designated. For example "° C." refers to degrees Celsius; "N" refers to normal or normality; "mol" refers to mole or moles; "eq" refers to equivalent; "g" refers to gram or grams; "h" refers to hour or hours; "HPLC" refers to high performance liquid chromatography; "min" refers to minute or minutes; "L" refers to liter or liters; "M" refers to molar or molarity; "brine" refers to a saturated aqueous sodium chloride solution; "MS" refers to mass spectrometry; "NMR" refers to nuclear magnetic resonance spectroscopy; "ppm" refers to parts per million; "RT" refers to room temperature; "TLC" refers to thin layer chromatography; "ACN" refers to acetonitrile; "DMF" refers to N,N-dimethylformamide; "DMSO" refers to dimethylsulfoxide; "Et$_2$O" refers to diethyl ether; "EtOAc" refers to ethyl acetate; "MeOH" refers to methanol; "EtOH" refers to ethanol; "iPrOH" refers to isopropanol; "TEA" refers to triethylamine; "TFA" refers to trifluoroacetic acid; "THF" refers to tetrahydrofuran.

EXAMPLES

Example 1

{2-[1-(3,5-bistrifluoromethylbenzyl)-5-pyridin-4-yl-1H-[1,2,3]triazol-4-yl]-pyridin-3-yl}-(2-chlorophenyl)-methanone (Form IV)

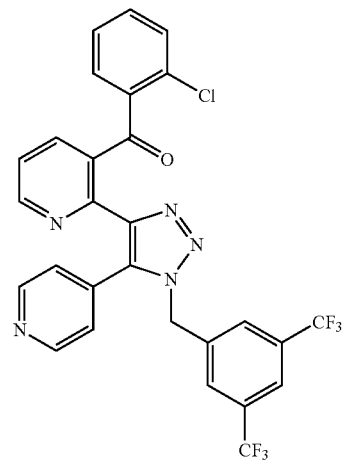

Add 1-azidomethyl-3,5-bistrifluoromethylbenzene (3.73 g, 13.8 mmol) and potassium carbonate (5.73 g, 41.4 mmol) to a solution of (2-chlorophenyl)-[2-(2-hydroxy-2-pyridin-4-yl-vinyl)pyridin-3-yl]methanone phosphate (6.0 g, 13.8 mmol) in DMSO (16 mL). Heat to 40° C. and stir for approximately 20-24 h. Cool the reaction mixture to ambient temperature, and add the mixture to CH$_2$Cl$_2$ (75 mL) and 1 N NaOH (75 mL). Separate the layers, and extract the aqueous layer with CH$_2$Cl$_2$ (50 mL). Separate the layers, combine the organic layers and extract the combined organic layers with 1 N NaOH (2×50 mL). Add MgSO$_4$ and acid-washed carbon (1.2 g), stir for 20 min and filter through Celite®. Concentrate the filtrate to a total weight of approximately 25 g. Add heptane (75 mL) dropwise over approximately 45 min. Seed the solution with the title compound if necessary. Stir the resulting slurry for 1 h and then filter to obtain the title compound. Dry the title compound, then add it to isopropanol (36 mL). Heat the mixture until the solid dissolves (approx. 65° C.). Allow the solution to cool to ambient temperature. Stir the resulting slurry for approximately 3 hours. Cool the slurry in an ice/water bath and stir for 2 h. Filter and dry to afford the title compound as a white solid. MS(IS) 588 (M+1). TLC (3% MeOH/CH$_2$Cl$_2$) R$_f$=0.17. $^1$H NMR (400 MHz, CDCl$_3$): 5.46 (s, 2H); 7.19 (m, 5H); 7.36 (dd, 1H, J=4.9, 7.8); 7.45 (s, 2H); 7.59 (m, 1H); 7.83 (s, 1H); 7.93 (dd, 1H, J=1.5, 7.8); 8.56 (dd, 1H, J=1.5, 4.9); 8.70 (d, 2H, J=5.9).

The reaction can also be carried out using (2-chlorophenyl)-[2-(2-hydroxy-2-pyridin-4-yl-vinyl)pyridin-3-yl]methanone (30.0 g; 72.3 mmol; 1.0 equiv) in isopropanol (225 mL). 1-azidomethyl-3,5-bistrifluoromethylbenzene (20.43 g; 76 mmol; 1.05 equiv) and potassium carbonate (5.0 g; 36.2 mmol; 0.5 equiv) are added, and the reaction mixture is heated to reflux for 21-24 hours. Cool the reaction mixture to 20° C., add water (120 mL), and stir for approximately 16 hours. Filter, wash with 120 mL isopropanol/ water (1:1 v/v), and dry under reduced pressure at 50° C. to yield the title compound, which may be recrystallized as described above.

Preparation 1-A (2-chlorophenyl)-[2-(2-hydroxy-2-pyridin-4-yl-vinyl)pyridin-3-yl]methanone

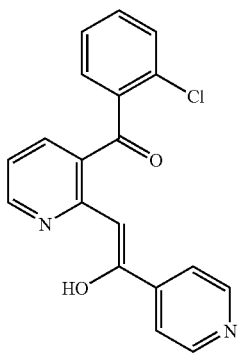

To a solution of (2-chloro-phenyl)-(2-fluoropyridin-3-yl) methanol (140 g, 0.59 mol) in dichloromethane (1.1 L) under an argon atmosphere, add 2,2,6,6-tetramethyl-1-piperidinyloxy (TEMPO) (1.43 g, 9.15 mmol) and potassium bromide (10% w/w in water, 57.1 mL, 0.048 mol). To the resulting mixture add a solution of sodium hypochlorite (13% w/w active chlorine in water, 403 mL, 0.85 mol) and sodium bicarbonate (20.3 g, 0.24 mol) in water (403 mL) while stirring vigorously and while maintaining the temperature below 20° C. Continue stirring the reaction mixture for 30 min or until the reaction is complete. Separate the layers, and concentrate the organic layer to approximately 200 mL total volume. Add dimethylsulfoxide and concentrate until no dichloromethane remains in the solution. Add 4-acetylpyridine (107 g, 0.88 mol) and powdered lithium hydroxide (28.2 g, 1.17 mol) and stir at 60° C. for 2.5 h or until the reaction is complete. Cool to ambient temperature and add dichloromethane (1.4 L) and an aqueous solution of 10% sodium chloride (1.3 L) while maintaining the temperature between 20° C. and 24° C. Separate the layers and extract the aqueous layer with dichloromethane (1.4 L). Separate the layers and combine the organic layers. Wash the combined organic layers with an aqueous solution of 10% sodium chloride (3×2.6 L). Concentrate the organic layer to approximately 500 mL total volume, then add methanol (1.0 L). Concentrate under vacuum until the weight of the resulting residue is approximately 500 g, then add more methanol (207 mL). Heat the solution to 60° C. When the temperature reaches 45° C., add phosphoric acid (85% w/w in water, 67.4 g, 0.58 mol). Stir the resulting slurry at 22° C. for 16 h. Collect the resulting solid by filtration and wash with methanol (3×65 mL) and water (3×65 mL). Add the resulting solid to a solution of potassium carbonate (49.3 g, 0.356 mol) in water (714 mL) and stir for 4 h. Collect the resulting solid by filtration, wash with water (50 mL) and dry under vacuum at 50° C. to afford the title compound as an orange solid. $^1$H NMR (400 MHz, DMSO-D$_6$) δ ppm 4.89 (s, 2H) 6.93 (d, J=7.33 Hz, 1H) 7.09 (s, 1H) 7.11-7.17 (m, 2H) 7.24 (dd, J=7.58, 5.31 Hz, 1H) 7.40-7.67 (m, 15H) 7.71-7.77 (m, 3H) 7.85 (d, J=7.83 Hz, 1H) 7.89 (d, J=6.06 Hz, 2H) 8.15 (d, J=7.58 Hz, 1H) 8.50 (d, J=3.79 Hz, 1H) 8.62 (d, J=3.79 Hz, 3H) 8.67 (d, J=5.81 Hz, 2H) 8.73 (dd, J=4.80, 1.52 Hz, 1H) 8.83 (d, J=5.81 Hz, 1H).

The title compound exists as a mixture of tautomers and geometric isomers. It is understood that each of these forms are encompassed within the scope of the invention.

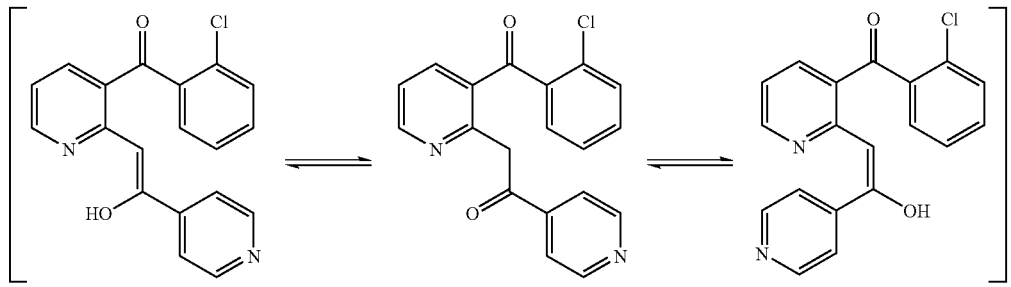

Preparation 1-B (2-chlorophenyl)-[2-(2-hydroxy-2-pyridin-4-yl-vinyl)pyridin-3-yl]methanone phosphate Under nitrogen, combine sodium tert-butoxide (8.99 g, 93.5 mmol), palladium acetate (0.36 g, 1.60 mmol), bis(2-diphenylphosphinophenyl)ether (1.06 g, 1.97 mmol), magnesium sulfate (4.68 g, 38.9 mmol) and toluene (160 mL). To this mixture add a solution of 4-acetylpyridine (7.60 g, 62.7 mmol) and (2-bromopyridin-3-yl)-(2-chlorophenyl) methanone (9.31 g, 31.4 mmol) in toluene (40 mL). Heat the reaction mixture to 60° C. and stir for 3 h. Cool the reaction mixture to ambient temperature. Add the reaction mixture to a solution of glacial acetic acid (9.3 mL) and water (40 mL). Stir for approximately 30 min and filter through Hyflo®. Separate the layers and extract the aqueous layer with toluene (50 mL). Add 1,3,5-triazine-2,4,6-trithiol (1.7 g) to the combined organic layers. Heat to 60° C. and stir for approximately 1 h. Allow the reaction mixture to cool to ambient temperature, add Darco® (2.3 g) and stir at ambient temperature for 1 h. Filter through Hyflo®, and concentrate the solution to an oil. Dissolve the resultant oil in n-butanol (38 mL) and methanol (93 mL) and heat to 60° C. Treat the solution with a mixture of 85% phosphoric acid (6.1 mL) in methanol (15 mL). Stir the mixture at 60° C. for approximately 1 h. Allow the mixture to cool to ambient temperature and stir for 13 h. Filter, rinse with methanol (26 mL) and dry to afford the title compound as an orange solid. LRMS (ES+) calcd for $C_{19}H_{14}ClN_2O_2$ (M+H$^+$) 337.06, found 337.31 m/z. IR (solid) 2364 (broad), 1658, 1561, 1278, 1152, 1108, 1050.

The title compound may also be prepared by an alternative process, which is described below. Add (2-phenylsulfonyl-pyridin-3-yl)-(2-chlorophenyl)methanone (15 g) and 4-acetylpyridine (7.59 g; 1.5 eq) to DMSO (150 mL) under an inert atmosphere of $N_2$. Heat the solution to 70° C., then add LiOH (4 g, 4 eq) in one portion. Stir the reaction mixture for 4 hours at that temperature. The mixture turns from red to dark brown during the reaction. Completion of the reaction may be checked by HPLC. After completion of the reaction, cool the reaction mixture to 15° C. with a cold-water bath, and add $CH_2Cl_2$ (150 mL). Quench the reaction mixture in 10 min with 10% NaCl (150 ml) containing acetic acid (9.58 mL; 4 eq). At the end of the addition, the temperature reaches approximately 27° C. Re-extract the aqueous layer with $CH_2Cl_2$ (150 ml). Combine the organic layers and wash with 10% NaCl (3×300 mL). Concentrate the combined organic layers to dryness under vacuum and re-dissolve the residue in MeOH (4.3 volumes). Cool the reaction mixture to 20° C., and add $H_3PO_4$ (85% w/w in water; 2.88 mL; 1 eq). Stir the suspension for 4 h at 20° C., filter, wash the precipitate with MeOH (2×15 mL) and dry under vacuum at 50° C. to yield the title compound as an orange solid.

The title compound exists as a mixture of tautomers and geometric isomers. It is understood that each of these forms are encompassed within the scope of the invention.

and wash the organic layer with $H_2O$ (25 mL). Concentrate the organic layer to approximately 2 total volumes. Add toluene (50 mL) and concentrate the solution to approximately 2 total volumes. Add toluene (65 mL) again, and concentrate the solution to approximately 2 total volumes. Add DMSO (18 mL). Add N,N-diisopropylethylamine (14.5 mL, 83.1 mmol) to the resulting solution. In a separate reaction vessel, dissolve sulfur trioxide pyridine complex (11.6 g, 72.7 mmol) in DMSO (50 mL). Add a portion of the sulfur trioxide pyridine complex/DMSO solution (35 mL) to the reaction mixture and stir for 30 min. Add a second portion of the sulfur trioxide pyridine complex/DMSO solution (9 mL) to the reaction mixture and stir for 30 min. Add a third portion of the sulfur trioxide pyridine complex/DMSO solution (9 mL) and stir for 30 min. Add a final portion of the sulfur trioxide pyridine complex/DMSO solution (approximately 9 mL) and stir for 30 min. Add ethyl acetate (50 mL) and 1 N HCl (100 mL). Separate the layers and extract the aqueous layer with ethyl acetate (25 mL). Separate the layers and extract the combined organic layers with $H_2O$ (25 mL). Separate the layers and concentrate the organic layer to approximately 2 total volumes. Add isopropanol (50 mL) and concentrate the resulting solution to approximately 2 total volumes. Add isopropanol (50 mL) and concentrate the resulting solution to approximately 2 total volumes. Add isopropanol (5 mL), and then add heptane (40 mL) dropwise. Stir the resulting slurry for 15 min. Cool the slurry to 0° C. and stir for 1 h. Filter the slurry, rinse the filter cake with chilled heptane (20 mL), and dry to afford the title compound as an off-white solid: $^1$H NMR (500 MHz, CDCl$_3$) δ 8.49 (dd, J=4.9, 2.0 Hz, 1H), 7.78 (dd, J=7.3, 2.0 Hz, 1H), 7.59 (dd, J=7.3, 1.5 Hz, 1H), 7.49-7.36 (m, 4H); $^{13}$C NMR (125 MHz, CDCl$_3$) δ 193.8, 152.0,

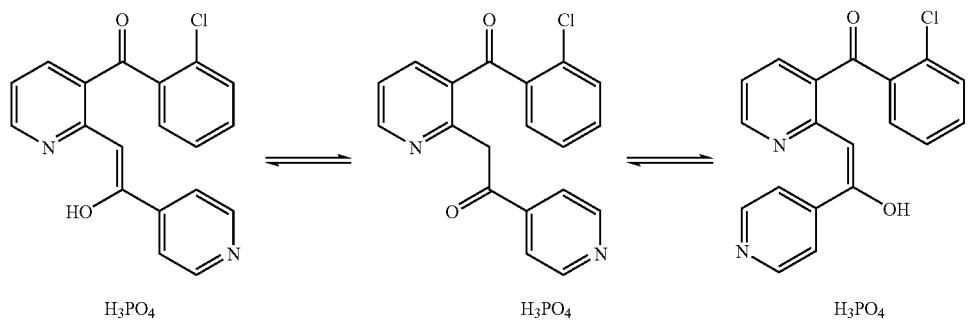

Preparation 1-C (2-bromopyridin-3-yl)-(2-chlorophenyl)methanone

Add n-butyllithium (21.7 mL, 34.8 mmol, 1.6 M in hexanes) to a –70° C. solution of diisopropylamine (4.9 mL, 34.8 mmol) in THF (75 mL). Allow the solution to cool back to –70° C., and add 2-bromopyridine (5.0 g, 31.6 mmol) to the solution while maintaining the temperature below –65° C. Rinse contents of vessel that contained 2-bromopyridine with THF (10 mL) and add this solution to the reaction mixture. Stir the resulting solution for 15 min, and then add a solution of 2-chlorobenzaldehyde (3.55 g, 31.6 mmol) in THF (15 mL) in a single portion. Stir the resulting solution for approximately 5 h at –70° C. Add MeOH (3.0 mL) and remove cooling. Add 3 N HCl (30 mL) to the reaction mixture followed by toluene (25 mL). Separate the layers, 139.5, 139.1, 137.7, 136.7, 133.6, 133.3, 131.8, 131.2, 127.4, 123.0. LRMS (ES+) calcd for $C_{12}H_8BrClNO$ (M+H$^+$) 295.9, found 295.8 m/z.

Preparation 1-D (2-Chlorophenyl)-(2-fluoropyridin-3-yl)-methanol

Add diisopropylamine-(286.6 g, 2.83 mol) to a –63° C. solution of n-butyllithium (2.47 M in hexanes, 917 mL, 2.27 mol) while maintaining the temperature below –38° C. Add tetrahydrofuran (1.20 L) while maintaining the temperature below –43° C. To the resulting solution add 2-fluoropyridine (200.0 g, 2.06 mol) while maintaining the temperature between –66° C. and –57° C. Stir the resulting solution between –72° C. and –57° C. for 45 min. To this solution add a solution of 2-chlorobenzaldehyde (318.5 g, 2.27 mol)

in tetrahydrofuran (125 mL) while maintaining the temperature between −70° C. and −39° C. Stir the resulting solution between −73° C. to −50° C. for 1 h, and then add methanol (198 g, 6.18 mol). Allow the solution to warm to −30° C. and stir for 30 min. Add the resulting solution to a −13° C. mixture of toluene (1.20 L) and 3 N hydrochloric acid (1.85 L, 5.55 mol). Separate the layers and extract the aqueous layer with toluene (1.2 L). Extract the combined organic layers with water (1.8 L), and then concentrate this solution at 60° C. under reduced pressure to an approximate weight of 910 g. Cool the solution to 25° C. Crystallization will occur. Stir the resulting slurry for 1 h. Add cyclohexane (2.0 L) over a period of 5 min, and then stir the resulting slurry for 14 h. Collect the resulting solid by filtration and wash the solid with cyclohexane (500 mL). Dry the solid under vacuum at 45° C. for 4 h to afford the title compound as a white solid. $^1$H NMR (400 MHz, DMSO-D$_6$) δ ppm 6.17 (d, J=4.80 Hz, 1H) 6.35 (d, J=4.80 Hz, 1H) 7.29-7.38 (m, 2H) 7.42 (t, J=7.71 Hz, 1H) 7.41-7.46 (m, 1H) 7.61-7.67 (m, 1H) 7.75-7.88 (m, 1H) 8.16 (d, J=4.55 Hz, 1H).

Preparation 1-E (2-phenylsulfonyl-pyridin-3-yl)-(2-chlorophenyl) methanone

To n-butyllithium (2.5 N in hexanes; 28 mL), which has been cooled to −65° C., add diisopropylamine while keeping the temperature between −65 and −52° C. A precipitation occurs. Add THF (42 mL) to the lithium diisopropylamine (LDA) suspension. To the suspension, add a solution of 2-phenylsulfonyl pyridine (14 g) in THF (42 mL) while maintaining the temperature between −65 and −55° C. Stir for approximately 15 min. A yellow to orange precipitate forms. Add a solution of 2-chlorobenzaldehyde (8.96 g) in THF (11 mL) to the suspension while keeping the temperature of the reaction mixture between −75 and −60° C. during the addition. A red solution is obtained. Stir the reaction mixture for 1 h at −70° C., then warm the reaction mixture to −30° C., followed by a careful addition of 3N HCl (112 mL). The temperature is allowed to reach 0° C. at the end of the addition. Warm the reaction mixture to approximately 20° C. and extract with toluene (2×140 mL).

Combine the organic layers, wash with water (100 mL) and concentrate to dryness under reduced pressure to yield a yellow solidifying oil. Dissolve the residue in CH$_2$Cl$_2$ (150 mL) and add a 10% KBr solution in water (44 mL) and 2,2,6,6-tetramethylpiperidin-1-oxyl (TEMPO) (728 mg). Cool the reaction mixture to 10° C. with an ice bath. Add a solution of 4% NaOCl (728 mL) and NaHCO$_3$ (6.5 g) under vigorous stirring and maintain the temperature around 10° C. during the addition. At the end of the addition, warm the reaction mixture to 20° C. and stir for 1 hour. The organic layer is decanted, separated and concentrated under vacuum to yield 25 g of crude oil. Dissolve the oily residue in DMF (100 mL) and slowly add water (160 mL) to precipitate the title compound. Stir the suspension for 1 hour at room temperature, then 15 minutes at 0° C. Filter the suspension, wash the precipitate with DMF/H$_2$O, and dry under vacuum at 50° C. to yield the title compound as a white to off-white solid. $^1$H NMR (600 MHz, CHLOROFORM-d) δ ppm 7.38 (td, J=7.52, 1.28 Hz, 1H) 7.47 (dd, J=7.80, 1.30 Hz, 1H) 7.51 (td, J=7.79, 1.60 Hz, 1H) 7.51 (t, J=7.89 Hz, 1H) 7.50-7.54 (m, J=7.75, 4.63 Hz, 1H) 7.60 (t, J=7.43 Hz, 1H) 7.73 (dd, J=7.75, 1.60 Hz, 1H) 7.81 (dd, J=7.79, 1.56 Hz, 1H) 8.00 (dd, J=8.44, 1.10 Hz, 2H) 8.76 (dd, J=4.63, 1.61 Hz, 1H).

Example 2

{2-[1-(3,5-bistrifluoromethylbenzyl)-5-pyridin-4-yl-1H-[1,2,3]triazol-4-yl ]-pyridin-3-yl}-(2-chlorophenyl)-methanone (Form IV)

Add (2-phenylsulfonyl-pyridin-3-yl)-(2-chlorophenyl) methanone (15 g) and 4-acetylpyridine (7.59 g; 1.5 eq) to DMSO (150 mL) under an inert atmosphere of N$_2$. Heat the solution to 70° C., then add LiOH (4 g; 4 eq) in one portion. Stir the reaction mixture for 4 hours and check for completion of the reaction by HPLC. The mixture turns from red to dark brown during the reaction. After completion of reaction, cool the reaction mixture to 15° C. and add CH$_2$Cl$_2$ (150 mL). Quench the reaction mixture with 10% NaCl (150 mL) containing acetic acid (9.58 mL; 4 eq). Separate the layers and re-extract the aqueous layer with CH$_2$Cl$_2$ (150 ml). Combine the organic layers and wash with 10% NaCl (3×300 mL). Concentrate the combined organic layers to dryness under vacuum and re-dissolve the residue in MeOH (4.3 volumes). Cool the reaction mixture to 20° C. and add H$_3$PO$_4$ (85% w/w in water; 2.88 mL; 1 eq). Stir the suspension for 4 h at 20° C., filter, and wash the precipitate with MeOH (2×15 mL).

To the wet precipitate suspended in water (35 mL), add THF (53 mL), K$_2$CO$_3$ (5.51 g; 1.5 eq) and stir the mixture for 10 min at ambient temperature. The mixture is allowed to decant and the layers are separated. Concentrate the organic layer to dryness, dissolve the residue in isopropyl alcohol (53 mL) and concentrate again. Re-dissolve the residue in isopropyl alcohol (53 mL), add 1-azidomethyl-3,5-bistrifluoromethylbenzene (5.23 mL; 1.05 eq) and K$_2$CO$_3$ (1.84 g) and heat the suspension to 82° C. for approximately 21 h. Check for completion of reaction by HPLC. Cool the reaction mixture to 20° C. and add water (35 mL) to precipitate. Filter, wash with isopropanol/water (1:1 v/v), and dry at 50° C. under reduced pressure to yield the title compound as a white to off-white solid.

Example 3

{2-[1-(3,5-bistrifluoromethylbenzyl)-5-pyridin-4-yl-1H-[1,2,3]triazol-4-yl ]-pyridin-3-yl}-(2-chlorophenyl)-methanone (Form IV)

A. {2-[1-(3,5-bistrifluoromethylbenzyl)-5-pyridin-4-yl-1H-[1,2,3]triazol-4-yl]-pyridin-3-yl}-(2-chlorophenyl)-methanone (400 mg) is dissolved in isopropanol (8 mL) at approximately 65° C. Cool the temperature to 54° C. and add H$_2$O (20 mL) to induce crystallization. The solid product is isolated by vacuum filtration.

B. Alternatively, {2-[1-(3,5-bistrifluoromethylbenzyl)-5-pyridin-4-yl-1H-[1,2,3]triazol 4-yl]-pyridin-3-yl}-(2-chlorophenyl)-methanone (600 mg) may be dissolved in isopropanol (4.5 mL) with heat. The solution is slowly cooled to RT, and the solid product may be isolated by vacuum filtration and washed with heptane.

C. In another method, {2-[1-(3,5-bistrifluoromethylbenzyl)-5-pyridin-4-yl-1H-[1,2,3]triazol-4-yl]-pyridin-3-yl}-(2-chlorophenyl)-methanone (400 mg) is dissolved in ethyl acetate (2 mL) with heat. The temperature is held at approximately 62° C., and heptane (10 mL) is added to induce crystallization. The product is isolated by vacuum filtration.

D. In another method, {2-[1-(3,5-bistrifluoromethylbenzyl)-5-pyridin-4-yl-1H-[1,2,3]triazol-4-yl]-pyridin-3-yl}-(2- chlorophenyl)-methanone (400 mg) is dissolved in ethyl acetate (4 mL) at RT. Heptane (15 mL) is added to induce crystallization, and the product is isolated by vacuum filtration.

E. In another method, {2-[1-(3,5-bistrifluoromethylbenzyl)-5-pyridin 4-yl-1H-[1,2,3]triazol-4-yl]-pyridin-3-yl}-(2-chlorophenyl)-methanone (300 mg) is dissolved in dichloromethane (2 mL) at RT. The temperature is raised to 40° C., at which time heptane (15 mL) is added to induce crystallization. The product is isolated by vacuum filtration.

Example 4

{2-[1-(3,5-bistrifluoromethylbenzyl)-5-pyridin-4-yl-1H-[1,2,3]triazol-4-yl ]-pyridin-3-yl}-(2-chlorophenyl)-methanone (Form V)

A. {2-[1-(3,5-bistrifluoromethylbenzyl)-5-pyridin-4-yl-1H-[1,2,3]triazol-4-yl]-pyridin-3-yl}-(2-chlorophenyl)-methanone (200 mg) is dissolved in hot MeOH (1 mL) or hot EtOH (2 mL). Water (10 mL) is added to the solution to induce crystallization at approximately 68 to 71° C. The suspension is cooled to RT, and the solid product is isolated by vacuum filtration.

B. Alternatively, {2-[1-(3,5-bistrifluoromethylbenzyl)-5-pyridin-4-yl-1H-[1,2,3]triazol-4-yl]-pyridin-3-yl}-(2-chlorophenyl)-methanone (200 mg) is dissolved in MeOH (7 mL) at RT. Water (10 mL) is added to the solution to induce crystallization. The solid product is isolated by vacuum filtration.

As used herein, the term "patient" refers to a mammal that is afflicted with one or more disorders associated with excess tachykinins. Guinea pigs, dogs, cats, rats, mice, horses, cattle, sheep, and humans are examples of mammals within the scope of the meaning of the term. It will be understood that the most preferred patient is a human. It is also understood that this invention relates specifically to the inhibition of mammalian NK-1 receptors.

It is also recognized that one skilled in the art may affect the disorders by treating a patient presently afflicted with the disorders or by prophylactically treating a patient afflicted with the disorders with an effective amount of the compound of Form IV, or Form V. Thus, the terms "treatment" and "treating" are intended to refer to all processes wherein there may be a slowing, interrupting, arresting, controlling, or stopping of the progression of the disorders described herein, and is intended to include prophylactic treatment of such disorders, but does not necessarily indicate a total elimination of all disorder symptoms.

As used herein, the term "effective amount" of a compound of the present invention refers to an amount that is effective in treating the disorders described herein.

The compounds of the present invention can be administered alone or in the form of a pharmaceutical composition, that is, combined with pharmaceutically acceptable carriers, or excipients, the proportion and nature of which are determined by the solubility and chemical properties of the compound selected, the chosen route of administration, and standard pharmaceutical practice.

Thus, the present invention provides pharmaceutical compositions comprising a compound of Form IV, or Form V, and a pharmaceutically acceptable diluent.

The compounds of the present invention can be administered by a variety of routes. In effecting treatment of a patient afflicted with disorders described herein, a compound of Form IV or Form V can be administered in any form or mode that makes the compound bioavailable in an effective amount, including oral and parenteral routes. For example, compounds of Form IV or Form V can be administered orally, by inhalation, or by the subcutaneous, intramuscular, intravenous, transdermal, intranasal, rectal, occular, topical, sublingual, buccal, or other routes. Oral administration is generally preferred for treatment of the neurological and psychiatric disorders described herein.

One skilled in the art of preparing formulations can readily select the proper form and mode of administration depending upon the particular characteristics of the compound selected, the disorder or condition to be treated, the stage of the disorder or condition, and other relevant circumstances. (*Remington's Pharmaceutical Sciences,* 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as povidone, hydroxypropyl cellulose, hydroxypropyl methyl cellulose, maltodextrin, microcrystalline cellulose, gum tragacanth or gelatin; excipients such as dicalcium phosphate, starch, mannitol or lactose; disintegrating agents such as alginic acid, Primogel®, croscarmellose sodium, corn starch and the like; lubricants such as talc, stearic acid, magnesium stearate or Sterotex®; glidants such as colloidal silicon dioxide; and sweetening agents, such as sucrose, aspartame, or saccharin, or a flavoring agent, such as peppermint, methyl salicylate or orange flavoring, may be added. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

In order to improve the solubility of the compounds of the present invention, preferred formulations for oral administration are those in which solubility of the compounds is enhanced by combination of the micronized compound with suitable excipients that enable ionic pair formation in combination with a proton donating source. Thus, a preferred formulation comprises an anionic surfactant and a suitable acid. Preferred anionic surfactants include, but are not limited to, sodium lauryl sulfate and dioctylsulfosuccinate sodium. Preferred acids include citric acid (anhydrous or monohydrate), succinic acid, and the like.

For the purpose of parenteral therapeutic administration, the compounds of the present invention may be incorporated into a solution or suspension. These preparations typically contain at least 0.001% of a compound of the invention, but may be varied to be between 0.001 and about 90% of the weight thereof. The amount of the compound of Form IV or Form V present in such compositions is such that a suitable dosage will be obtained. The solutions or suspensions may also include one or more of the following adjuvants: sterile diluents, such as water for injection, saline solution, fixed oils, polyethylene glycols, glycerine, propylene glycol or other synthetic solvents; antibacterial agents, such as benzyl alcohol or methyl paraben; antioxidants, such as ascorbic acid or sodium bisulfite; chelating agents, such as ethylene diaminetetraacetic acid; buffers, such as acetates, citrates or phosphates; and agents for the adjustment of tonicity, such as sodium chloride or dextrose. The parenteral preparation can be enclosed in ampoules, disposable syringes or multiple dose vials made of glass or plastic. Preferred compositions and preparations may be determined by one skilled in the art.

The compounds of the present invention may also be administered topically, and when done so, the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical formulations may contain a concentration of a compound of Form IV or Form V from about 0.1 to about 10% w/v (weight per unit volume).

The following formulation example is illustrative and is not intended to limit the scope of the present invention.

Formulation 1
Form IV hard-gelatin capsules

| Ingredient | Quantity (mg/capsule) | | |
|---|---|---|---|
| Form IV | 1.00 | 10.00 | 100.00 |
| Mannitol | 295.13 | 286.71 | 202.65 |
| Microcrystalline Cellulose (inside) | 52.08 | 50.60 | 35.76 |
| Microcrystalline Cellulose (outside) | 19.35 | 19.35 | 19.35 |
| Sodium Laurylsulfate (inside) | 0.09 | 0.49 | 4.95 |
| Sodium Laurylsulfate (outside) | 0.00 | 0.49 | 4.95 |
| Hydroxypropylcellulose | 12.91 | 12.91 | 12.91 |
| Citric Acid | 32.25 | 32.25 | 32.25 |
| Colloidal Silicon Dioxide | 4.30 | 4.30 | 4.30 |
| Croscarmellose Sodium | 8.60 | 8.60 | 8.60 |
| Stearic Acid | 4.30 | 4.30 | 4.30 |

Typically, the drug substance is in a micronized form and is combined with fillers, buffer, surfactant, and disintegrant. The formulation is wet-granulated with the binder solution in a high-shear mixer or alternatively, in a fluid-bed granulator. The drug substance is mixed with the excipients of the inner granule phase (mannitol, microcrystalline cellulose, citric acid, sodium laurylsulfate, hydroxypropylcellulose) and then granulated with the binder solution, typically comprising hydroxypropylcellulose and sodium laurylsulfate.

Alternatively, a direct compaction or compression process may be applied. After appropriate drying in a fluid-bed dryer or a tray oven, the granules are typically sieved through an appropriate screen (e.g., 1016 μm) and combined with the lubricant (stearic acid), glidant (colloidal silicon dioxide), filler (microcrystalline cellulose), and surfactant (sodium laurylsulfate) in a mixer. The mixture is blended for approximately 5 min.

The final mixture can be filled into size 0 hard-gelatin, HPMC, starch or other suitable capsules or formed into tablets.

In one embodiment, the present invention provides methods of treating disorders selected from the group consisting of anxiety (including generalized anxiety disorder, panic disorder, obsessive compulsive disorder, and social phobia or social anxiety disorder), depression (including major depressive disorder), psychosis, schizophrenia and other psychotic disorders, such as bipolar disorder, neurodegenerative disorders (including senile dementia of the Alzheimer's type, Alzheimer's disease, AIDS-associated dementia, and Down's syndrome), seizure disorders (including generalized and partial seizures), demyelinating diseases (including multiple sclerosis and amyotrophic lateral sclerosis), neuropathological disorders (including peripheral neuropathy, diabetic and chemotherapy-induced neuropathy, and post-herpetic and other neuralgias), acute and chronic obstructive airway diseases (including adult respiratory distress syndrome, bronchopneumonia, bronchospasm, chronic bronchitis, drivercough, and asthma), inflammatory diseases (including inflammatory bowel disease, psoriasis, fibrositis, osteoarthritis, and rheumatoid arthritis), disorders of the musculo-skeletal system (such as osteoporosis), allergies (including eczema and rhinitis), hypersensitivity disorders (such as poison ivy), ophthalmic diseases (such as conjunctivitis, vernal conjunctivitis, and the like), cutaneous diseases (including contact dermatitis, atopic dermatitis, urticaria, or other forms of eczematoid dermatitis), addiction disorders (including alcoholism), stress-related somatic disorders, reflex sympathetic dystrophy (such as shoulder/hand syndrome), dysthymic disorders, adverse immunological reactions (such as rejection of transplanted tissues), disorders related to immune enhancement or suppression (such as systemic lupus erythematosis), gastrointestinal disorders, diseases associated with the neuronal control of viscera (such as ulcerative colitis, Crohn's disease, functional dyspepsia and irritable bowel syndrome); disorders of bladder function (such as bladder detrusor hyper-reflexia and incontinence, including urge incontinence), atherosclerosis, fibrosis and collagen diseases (such as scleroderma and eosinophilic fascioliasis), irritative symptoms of benign prostatic hypertrophy, disorders associated with blood pressure (such as hypertension), disorders of blood flow caused by vasodilation or vasospastic diseases (such as angina, migraine, and Reynaud's disease), hot flushes (hot flashes), emesis (including chemotherapy-induced nausea and acute or delayed emesis), and pain or nociception (including that attributable to or associated with any of the foregoing conditions), comprising: administering to a patient in need thereof an effective amount of a compound of Form IV or Form V. That is, the present invention provides methods of treating disorders associated with an excess of tachykinins, comprising: administering to a patient in need thereof an effective amount of a compound of Form IV or Form V.

The present invention contemplates the various disorders described to be treated herein and others that can be treated by such antagonists, as appreciated by those skilled in the art.

The disorders associated with an excess of tachykinins are treated by administering an effective amount of a compound or pharmaceutical composition of Form IV or Form V. An effective amount can be readily determined by the attending diagnostician, as one skilled in the art, by the use of conventional techniques and by observing results obtained under analogous circumstances. In determining an effective amount, the dose of a compound of Form IV or Form V, a number of factors are considered by the attending diagnostician, including, but not limited to: the species of mammal—its size, age, and general health; the specific disorder involved; the degree of involvement or the severity of the disorder; the response of the individual patient; the mode of administration; the bioavailability characteristics of the preparation administered; the dose regimen selected; the use of other concomitant medication; and other relevant circumstances.

An effective amount of a compound of the present invention is expected to vary from about 0.001 milligram per kilogram of body weight per day (mg/kg/day) to about 100 mg/kg/day. Preferred amounts may be readily determined by one skilled in the art.

Of the disorders associated with an excess of tachykinins that are treated according to the present invention, the treatment of depression, anxiety, inflammatory bowel disease, irritable bowel syndrome (including constipation-predominant, diarrhea-predominant, and mixed irritable bowel syndrome), and emesis (chemotherapy-induced nausea and acute or delayed emesis) are particularly preferred.

In a preferred embodiment, the present invention provides a method for treating major depressive disorder, comprising: administering to a patient in need thereof an effective amount of a compound, which is {2-[1-(3,5-bistrifluoromethylbenzyl)-5-pyridin-4-yl-1H-[1,2,3]triazol-4-yl]-pyridin-3-yl}-(2-chlorophenyl)-methanone (Form IV).

In another preferred embodiment, the present invention provides a method for treating generalized anxiety disorder, comprising: administering to a patient in need thereof an effective amount of a compound, which is {2-[1-(3,5-bistrifluoromethylbenzyl)-5-pyridin-4-yl-1H-[1,2,3]triazol-4-yl]-pyridin-3-yl}-(2-chlorophenyl)-methanone (Form IV).

In another preferred embodiment, the present invention provides a method for treating panic disorder, comprising: administering to a patient in need thereof an effective amount of a compound, which is {2-[1-(3,5-bistrifluoromethylbenzyl)-5-pyridin-4-yl-1H-[1,2,3]triazol-4-yl]-pyridin-3-yl}-(2-chlorophenyl)-methanone (Form IV).

In another preferred embodiment, the present invention provides a method for treating obsessive compulsive disorder, comprising: administering to a patient in need thereof an effective amount of a compound, which is {2-[1-(3,5-bistrifluoromethylbenzyl)-5-pyridin-4-yl-1H-[1,2,3]triazol-4-yl]-pyridin-3-yl}-(2-chlorophenyl)-methanone (Form IV).

In another preferred embodiment, the present invention provides a method for treating social phobia or social anxiety disorder, comprising: administering to a patient in need thereof an effective amount of a compound, which is {2-[1-(3,5-bistrifluoromethylbenzyl)-5-pyridin-4-yl-1H-[1,2,3]triazol-4-yl]-pyridin-3-yl}-(2-chlorophenyl)-methanone (Form IV).

In another preferred embodiment, the present invention provides a method for treating irritable bowel syndrome, comprising: administering to a patient in need thereof an effective amount of a compound, which is {2-[1-(3,5-bistrifluoromethylbenzyl)-5-pyridin-4-yl-1H-[1,2,3]triazol-4-yl]-pyridin-3-yl}-(2-chlorophenyl)-methanone (Form IV).

In another preferred embodiment, the present invention provides a method for treating major depressive disorder, comprising: administering to a patient in need thereof an effective amount of a compound, which is {2-[1-(3,5-bistrifluoromethylbenzyl)-5-pyridin-4-yl-1H-[1,2,3]triazol-4-yl]-pyridin-3-yl}-(2-chlorophenyl)-methanone (Form V).

In another preferred embodiment, the present invention provides a method for treating generalized anxiety disorder, comprising: administering to a patient in need thereof an effective amount of a compound, which is {2-[1-(3,5-bistrifluoromethylbenzyl)-5-pyridin-4-yl-1H-[1,2,3]triazol-4-yl]-pyridin-3-yl}-(2-chlorophenyl)-methanone (Form V).

In another preferred embodiment, the present invention provides a method for treating panic disorder, comprising: administering to a patient in need thereof an effective amount of a compound, which is {2-[1-(3,5-bistrifluoromethylbenzyl)-5-pyridin-4-yl-1H-[1,2,3]triazol-4-yl]-pyridin-3-yl}-(2-chlorophenyl)-methanone (Form V).

In another preferred embodiment, the present invention provides a method for treating obsessive compulsive disorder, comprising: administering to a patient in need thereof an effective amount of a compound, which is {2-[1-(3,5-bistrifluoromethylbenzyl)-5-pyridin-4-yl-1H-[1,2,3]triazol-4-yl]-pyridin-3-yl}-(2-chlorophenyl)-methanone (Form V).

In another preferred embodiment, the present invention provides a method for treating social phobia or social anxiety disorder, comprising: administering to a patient in need thereof an effective amount of a compound, which is {2-[1-(3,5-bistrifluoromethylbenzyl)-5-pyridin-4-yl-1H-[1,2,3]triazol-4-yl]-pyridin-3-yl}-(2-chlorophenyl)-methanone (Form V).

In another preferred embodiment, the present invention provides a method for treating irritable bowel syndrome, comprising: administering to a patient in need thereof an effective amount of a compound, which is {2-[1-(3,5-bistrifluoromethylbenzyl)-5-pyridin-4-yl-1H-[1,2,3]triazol-4-yl]-pyridin-3-yl}-(2-chlorophenyl)-methanone (Form V).

Disorders of the central nervous system, including depressive and anxiety disorders, have been characterized in the Diagnostic and Statistical Manual of Mental Disorders (DSM-IV™) (1994, American Psychiatric Association, Washington, D.C.). The DSM-IV™ provides clear descriptions of diagnostic categories. The skilled artisan will recognize that there are alternative nomenclatures, nosologies, and classification systems for these disorders, and that these systems may evolve with medical scientific progress. For instance, the ICHPPC-2 (International Classification of Health Problems in Primary Care) ($3^{rd}$ edition, 1983, Oxford University Press, Oxford) provides an alternative classification system. Thus, the terms "depression," "depressive disorders," "anxiety," and "anxiety disorders" are intended to include like disorders that are described in other diagnostic sources.

According to the fourth edition of the DSM-IV™, major depressive disorders are characterized by one or more major depressive episodes, which consist of a period of at least two weeks of depressed mood or loss of pleasure, in addition to other symptoms. Thus, the skilled artisan will recognize that the present invention is useful for the treatment of either a single episode or recurrent episodes of major depressive disorder.

The skilled artisan will appreciate that other depressive disorders may also be treated by administering an effective amount of a compound of the present invention. Such other depressive disorders include dysthymic disorder, and depressive disorders not otherwise specified (for example, premenstrual dysphoric disorder, minor depressive disorder, recurrent brief depressive disorder, or postpsychotic depressive disorder of schizophrenia). In addition, the treatment of depression by the compounds of the present invention may also include the treatment of mood disorders due to a general medical condition and substance-induced mood disorders.

The DSM-IV™ also provides a diagnostic tool for anxiety and related disorders. These disorders include: panic disorder with or without agoraphobia, agoraphobia without history of panic disorder, specific phobia, social phobia or social anxiety disorder, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein, the term "anxiety" includes treatment of those anxiety disorders and related disorders described in the DSM-IV.

What is claimed is;

1. A crystalline Form IV {2-[1-(3,5-bistrifluoromethylbenzyl)-5-pyridin-4-yl-1H-[1,2,3]triazol-4-yl]-pyridin-3-yl}-(2-chlorophenyl)-methanone characterized by at least one of the following:
   a) a solid-state $^{13}C$ nuclear magnetic resonance spectrum comprising peaks at the following chemical shifts: 52.3±0.2 and 195.4±0.2 ppm;
   b) an X-ray powder diffraction pattern comprising at least two peaks wherein one peak is 12.1±0.1°, and the second peak is selected from the group consisting of 8.3=0.1°, 14.3±0.1°, 16.6±0.1°, 16.9±0.1°, and 18.5±0.1in 2θ; and
   c) an X-ray powder diffraction pattern comprising at least the following peaks: 8.3±0.1°, 12.1±0.1°, 16.6±0.1°, 16.9±0.1°, and 18.5±0.1° in 2θ.

2. A crystalline Form V {2-[1-(3,5-bistrifluoromethylbenzyl) -5 -pyridin-4-yl-1H-[1,2,3]triazol-4-yl]-pyridin-3-yl}-(2-chlorophenyl) -methanone characterized by at least one of the following:
   a) a solid-state $^{13}C$ nuclear magnetic resonance spectrum comprising peaks at the following chemical shifts: 54.3±0.2 and 196.6±0.2 ppm;
   b) an X-ray powder diffraction pattern comprising at least two peaks wherein one peak is 12.5±0.1°, and the second peak is selected from the group consisting of 15.8±0.1°, 16.5±0.1°, 19.1±0.1°, 19.7±0.1°, 21.5±0.1°, 25.3±0.1°, 27.7±0.1° and 28.6±0.1° in 2θ; and
   c) an X-ray powder diffraction pattern comprising at least the following peaks: 12.5±0.1°, 25.3±0.1°, 27.7±0.1°, and 28.6±0.1° in 2θ.

3. A process for preparing a compound that is {2-[1-(3, 5-bistrifluoromethylbenzyl) -5-pyridin-4-yl-1H-[1,2,3]triazol-4-yl]-pyridin-3-yl}-(2-chlorophenyl) -methanone, comprising reacting (2-chlorophenyl)-[2-(2-hydroxy-2-pyridin-4-yl-vinyl) pyridin-3-yl]methanone or a phosphate salt thereof with 1-azidomethyl-3,5-bistrifluoromethylbenzene in the presence of a suitable base and a solvent.

4. The process of claim 3 wherein the base is potassium carbonate.

5. The process of claim 4 wherein the solvent is selected from the group consisting of dimethylsulfoxide, isopropanol, ethanol, tetrahydrofuran, and toluene.

6. A process for preparing the compound of claim 1 comprising crystallization of {2-[1-(3,5-bistrifluoromethylbenzyl)-5-pyridin-4-yl-1H-[1,2,3]triazol-4-yl]-pyridin-3-yl}-(2-chlorophenyl)-methanone from a solvent.

7. The process of claim 6 wherein the solvent is selected from the group consisting of isopropanol, acetone, acetonitrile, propanol, butanol, ethyl acetate, methyl tertiary butyl ether, and dichloromethane.

8. A process for preparing the compound of claim 1 comprising crystallization of {2-[1-(3,5-bistrifluoromethylbenzyl)-5-pyridin-4-yl-1H-[1,2,3]triazol-4-yl]-pyridin-3-yl}-(2-chlorophenyl)-methanone by solution-mediated phase transformation.

9. A process for preparing the compound of claim 2 comprising crystallization of {2-[1-(3,5-bistrifluoromethylbenzyl)-5-pyridin-4-yl-1H-[1,2,3]triazol-4-yl]-pyridin-3-yl}-(2-chlorophenyl)-methanone from a mixture of a solvent and an anti-solvent.

10. The process of claim 9 wherein the solvent is methanol or ethanol.

11. The process of claim 10 wherein the anti-solvent is water.

12. A solid pharmaceutical composition comprising a crystalline compound of claim 1, in combination with one or more pharmaceutically acceptable carriers, excipients, or diluents.

13. The composition of claim 12 comprising at least one of the following: mannitol, microcrystalline cellulose, hydroxypropylcellulose, colloidal silicon dioxide, croscarmellose sodium, and stearic acid.

14. The composition of claim 13 further comprising an anionic surfactant in combination with an acid.

15. The composition of claim 14 wherein the anionic surfactant is sodium laurylsulfate and wherein the acid is citric acid.

16. A solid pharmaceutical composition comprising a crystalline compound of claim 2, in combination with one or more pharmaceutically acceptable carriers, excipients, or diluents.

17. The composition of claim 16 comprising at least one of the following: mannitol, microcrystalline cellulose, hydroxypropylcellulose, colloidal silicon dioxide, croscarmellose sodium, and stearic acid.

18. The composition of claim 17 further comprising an anionic surfactant in combination with an acid.

19. The composition of claim 18 wherein the anionic surfactant is sodium laurylsulfate and wherein the acid is citric acid.

* * * * *

UNITED STATES PATENT AND TRADEMARK OFFICE
CERTIFICATE OF CORRECTION

PATENT NO. : 7,381,826 B2
APPLICATION NO. : 10/574712
DATED : June 3, 2008
INVENTOR(S) : Alfio Borghese et al.

It is certified that error appears in the above-identified patent and that said Letters Patent is hereby corrected as shown below:

Column 23, line 28 reads "8.3=0.1°...," should read --8.3±0.1°...--

Signed and Sealed this

Third Day of November, 2009

David J. Kappos
*Director of the United States Patent and Trademark Office*